United States Patent [19]

Adams et al.

[11] 3,957,435

[45] May 18, 1976

[54] PASSIVE HEMAGGLUTINATION TEST METHOD AND COMPOSITION FOR USE THEREIN

[75] Inventors: Ernest Clarence Adams; Howard Raymond Teeter, both of Elkhart, Ind.

[73] Assignee: Miles Laboratories, Inc., Elkhart, Ind.

[22] Filed: Dec. 12, 1974

[21] Appl. No.: 531,974

[52] U.S. Cl. .............................. 23/230 B; 424/12
[51] Int. Cl.² ........................................ G01N 33/16
[58] Field of Search ............. 23/230 B; 424/12, 85, 424/88; 252/408

[56] References Cited
UNITED STATES PATENTS

| | | | |
|---|---|---|---|
| 3,171,783 | 3/1965 | Fisk | 23/230 B |
| 3,236,732 | 2/1966 | Arquilla | 23/230 B |
| 3,278,270 | 10/1966 | Fossel | 23/230 B |
| 3,298,787 | 1/1967 | Fossel | 23/230 B |
| 3,345,138 | 10/1967 | Eberhard | 23/230 B |
| 3,446,598 | 5/1969 | Yoder | 23/230 B |

FOREIGN PATENTS OR APPLICATIONS 979,759  1/1965  United Kingdom

OTHER PUBLICATIONS

Chemical Abstracts, 77:160631z (1972).

*Primary Examiner*—Morris O. Wolk
*Assistant Examiner*—Sidney Marantz
*Attorney, Agent, or Firm*—Andrew L. Klawitter

[57] ABSTRACT

An immunological test composition containing a passive hemagglutination indicator and a ferric-specific chelating agent for detecting an antigen or an antibody in a fluid sample such as urine. The test composition applies to both direct hemagglutination and hemagglutination inhibition tests. The ferric-specific chelating agent may be any of phenanthroline, apoferritin, transferrin, deferoxamine and N,N-bis-2-hydroxyethylglycine.

28 Claims, No Drawings

PASSIVE HEMAGGLUTINATION TEST METHOD AND COMPOSITION FOR USE THEREIN

BACKGROUND OF THE INVENTION

1. Field of the Invention

This invention relates to means for detecting an antigen or an antibody in a fluid sample based on passive hemagglutination. In one aspect, the present invention relates to the detection of chorionic gonadotropin in a urine specimen and therefore finds particular application in the detection of pregnancy.

Hemagglutination may be generally referred to as the clumping or aggregation of red blood cells. The clumping or aggregation of erthrocytic carrier particles which are incorporated with an immunochemically active substance in the presence of an appropriate immunochemical counterpart is referred to as passive hemagglutination. As used herein, the term immunochemically active substance refers to one member of the group consisting of an antigen or an antibody thereto and the term immunochemical counterpart refers to the other member.

There are basically two immunological test methods involving passive hemagglutination, direct passive hemagglutination tests and passive hemagglutination inhibition tests. Both methods involve the use of a passive hemagglutination indicator which comprises an erythrocytic carrier particle having an immunochemically active substance attached thereto. The indicator is fabricated such that passive hemagglutination will occur when an immunochemical counterpart to the carrier-incorporated immunochemically active substance is contacted with the indicator.

In direct passive hemagglutination tests, the presence of an immunochemically active substance in a sample may be determined by combining, in a vessel having a concave bottom, a quantity of sample to be tested and a passive hemagglutination indicator which comprises the immunochemical counterpart. If present, the immunochemically active substance reacts with the carrier-incorporated counterpart to form a smooth, substantially homogeneous, hemagglutination deposit. In the absence of the immunochemically active substance, the indicator settles to form a visible disc or ring on the bottom of the test vessel.

In passive hemagglutination inhibition tests, the presence of an immunochemically active substance in a sample may be determined by combining, in a vessel having a concave bottom, a predetermined quantity of the counterpart, and a passive hemagglutination indicator which comprises the immunologically active substance to be determined. Since the affinity of the counterpart for the immunochemically active substance free in solution is greater than its affinity for the immunochemically active substance incorporated with the carrier, hemagglutination will occur only when the substance to be determined is present in the sample in an amount less than that capable of reacting with all of the counterpart present. Thus, in contrast to the direct method, the presence of the substance to be determined, rather than its absence, is indicated by the appearance of a visible ring or disc comprised of settled indicator particles.

2. Description of the Prior Art

It is well known that conventional passive hemagglutination inhibition test systems are characterized as having an unacceptable level of false negative results. In reading the test results, the lack of appearance of a visible indicator sediment due to the occurrence of hemagglutination is recorded as a negative result. Theoretically, where there is a sufficient amount of the immunochemically active substance to be determined in the sample tested to react with the quantity of counterpart present, hemagglutination should not occur as there would be no free counterpart available to react with the hemagglutination indicator. However, it has been found that hemagglutination may occur even where there is no available free counterpart, that is, where there is a sufficient level of the substance to be determined in the sample to bind all the free counterpart. Such spontaneous or non-specific hemagglutination therefore yields a false negative result.

The problem of false negative results in passive hemagglutination inhibition test systems for detecting gonadotropins in urine has been previously recognized in British Pat. No. 979,759. It was suggested that the cause of spontaneous agglutination was an excess of calcium ions. The hypothesis was that the incidence of false negative results is a function of the age of the urine specimen tested, since the observation was made that calcium ion level increased with the age of the urine. The solution proposed in British Pat. No. 979,759 was to carry out the test reaction in the presence of a calcium chelating agent in order to bind all the calcium ions present in the test sample and thereby to prevent calcium ion-induced, non-specific agglutination. The preferred chelating agents proposed were ethylenediamine tetraacetic acid, citric acid and its alkali metal and ammonium salts.

SUMMARY OF THE INVENTION

It has now been found that the incidence of false negatives may be reduced substantially by carrying out the passive hemagglutination test reaction in the presence of a ferric-specific chelating agent which has a low affinity for binding with calcium ions. In accordance with the present invention, therefore, there is provided a method for detecting an immunochemically active substance in a fluid sample which comprises contacting the fluid sample to be tested with an appropriate passive hemagglutination indicator, and with an immunological counterpart of said substance to be determined if an inhibition method is to be followed, to form a reaction mixture, the improvement which comprises including a ferric-specific chelating agent in said reaction mixture. Where a direct passive hemagglutination method is followed, the passive hemagglutination indicator includes the counterpart. On the other hand, where an inhibition method is followed, the indicator includes the substance to be determined. Accordingly, an immunochemically active substance may be detected using an improved passive hemagglutination inhibition test composition comprising an immunochemical counterpart; a passive hemagglutination indicator, which includes said substance to be determined; and a ferric-specific chelating agent. Also, an immunochemically active substance may be detected using an improved direct passive hemagglutination test composition comprising a passive hemagglutination indicator, which includes an immunological counterpart, and a ferric-specific chelating agent.

DESCRIPTION OF THE PREFERRED EMBODIMENTS

In accordance with the teachings of the present invention it is hypothesized that during the stages of collection and storage of erythrocytes and during the preparation of formalinized erythrocytes and of the passive hemagglutination indicator conjugate, a small amount of hemoglobin is released from within the erythrocyte cell. The released hemoglobin apparently becomes attached or associated with the erythocyte cell surface and thereafter undergoes degradation to its heme derivative and ferric ion. It is theorized that under certain environmental conditions the presence of ferric ion causes conjugation between erythrocyte cells resulting in hemagglutination. Such spontaneous, non-specific hemagglutination produces a false positive result in a direct test and a false negative result in an inhibition test.

It has been found that such non-specific hemagglutination is substantially eliminated by binding or otherwise tying up the endogenous ferric ion to prevent it from interacting with the erythrocytes to form a hemagglutination complex. Inhibition of the apparent ferric ion-induced, nonspecific hemagglutination is conveniently accomplished by contacting the passive hemagglutination indicator with a ferric-specific chelating agent.

A ferric-specific chelating agent may be defined as a chelating agent which, if present in a sufficient amount, binds with substantially all of the ferric ions present in an aqueous sample, but does not bind with a substantial number of the calcium ions present. British Pat. No. 979,759 teaches that all of the calcium ions present in the reaction mixture should be bound by the chelating agent. In contradistinction, it has been found that in order to obtain reliable results, a certain quantity of calcium ions must be present in the reaction mixture. Thus, the use of a ferric-specific chelating agent is in contrast to the prior art teachings.

Substances which may be classified as ferric-specific chelating agents may be more particularly defined as those chelating agents for whom the expression $$\frac{\log K_{Fe}+3}{\log K_{Ca}+2}$$

is greater than about 7. In this expression $K_{Fe}+3$ and $K_{Ca}+2$ are the equilibrium constants for the formation of the complexes formed by the chelating agent with ferric ion and calcium, respectively. Thus, it is those chelating agents which possess a $10^7$ or greater affinity for ferric ion over calcium ion which are preferred. The logarithm of the formation constant is referred to as the stability constant. As shown in the table below listing well known chelating agents, the preferred chelating agents are phenanthroline, apoferritin, transferrin, deferoxamine, and N,N-bis-2-hydroxyethylglycine.

| Chelating Agent | $\log K_{Fe}+3$ | $\log K_{Ca}+2$ | $\frac{\log K_{Fe}+3}{\log K_{Ca}+2}$ |
|---|---|---|---|
| o-phenanthroline | 14.1[1] | 0.7[1] | 20.1 |
| transferrin | 26.0[2] | <1[3] | >26.0 |
| apoferritin | >26.0[2] | <1[3] | >26.0 |
| deferoxamine | 30.7[4] | 1.7[4] | 18.1 |
| N,N-bis-2-hydroxyethylglycine | 30.1[4] | 3.8[5] | 10.8 |
| ethylenediamine tetraacetic acid | 24.0[4] | 10.6[4] | 2.3 |
| citric acid | 11.7[6] | 4.84[6] | 2.4 |

[1]Martel, A.E., Stability Constants of Metal-Ion Complexes, Section II Organic Ligands, Special Publication No. 17, The Chemical Society, London (1964) pp. 664 & 665.
[2]Saltman, P. et al., Metal-Binding in Medicine, ed. Seven, M.F. et al., Lippincott (Philadelphia, 1960) pp. 241244.
[3]estimated to be less than 1 due to biological specificity.
[4]Amer. Scient. 54:586 (1971).
[5]Biochem. 5:467 (1966).
[6]Martel, A.E., ibid pp. 478 & 479.

The values of the stability constants for ethylenediamine tetraacetic acid and citric acid are pH dependent and in the above table have been selected for that pH which yields stability constants for which the ratio log $K_{Fe}+3$ to log $K_{Ca}+2$ is the maximum.

The hypothesized leaking of hemoglobin from erythrocytes during the preparation, storage, and use of passive hemagglutination indicators and the subsequent non-specific hemagglutination due to the presence of the hemoglobin degradation product ferric ion apparently occurs when the erythrocytes are placed in a liquid environment, particularly when placed in the form of an aqueous dispersion or suspension. Thus, unless the hemagglutination indicator is in a solid or dry form, such as a lyophilized form, spontaneous hemagglutination may occur in the absence of a ferric-specific chelating agent. Therefore, the present invention provides a stabilized passive hemagglutination indicator in a liquid environment.

Preferably, however, the indicator component of the reaction mixture is in a dry form and therefore stable relative to non-specific agglutination until added to the reaction mixture. Therefore, inhibition of spontaneous agglutination is generally accomplished according to the present invention by contacting the reaction mixture with the ferric-specific chelating agent.

One method of contacting the reaction mixture with the ferric-specific chelating agent according to the present invention is by directly adding to the mixture an appropriate amount of the chelating agent. The chelating agent may be in the form of a solid or in aqueous solution. Another method is by mixing an appropriate amount of the chelating agent with one or more of the components of the reaction mixture, either singly or in any combination, prior to the formation of the reaction mixture itself.

The indicator component, or the free counterpart component or both where an inhibition method is to be followed, may be in the form of a liquid, such as an aqueous solution or suspension, or in a solid or dried form, such as lyophilized form. When any component of the reaction mixture is in a solid or dried form, the chelating agent may be incorporated therewith by mixing the component with the chelating agent and lyophilizing or otherwise drying the mixture.

When following an inhibition method, the free counterpart and the indicator are preferably kept separated until the reaction mixture is formed. If prematurely combined, the counterpart and the sensitized indicator will become reversibly bound together even when in a lyophilized state, thereby increasing the required inhibition reaction time. The lyophilized counterpart and indicator components may be conveniently disposed in separate wells of a reaction capsule constructed such that upon adding the liquid test sample to the capsule, the reaction mixture can be formed simply by shaking the capsule. The preparation and use of such a capsule is described in the examples which follow.

According to the teachings of the present invention, non-specific agglutination of passive hemagglutination indicators is due to the release of ferric ions from erythrocytes. Therefore, the use of a ferric-specific chelating agent according to the present invention is applicable to any conventional immunological indicator which comprises an immunochemically active substance attached to a carrier material and which is capable of participating in passive hemagglutination independent of whether a direct or an inhibition test method is to be followed. The carrier material generally is either red blood cells or treated red blood cells, such as formalinized red blood cells. In the formation of the immunological indicator or reagent, the desired immunochemically active substance may be covalently bound to the carrier material either directly or indirectly through a coupling agent, for example, as described in *Ann. Clin. Lab. Sci.* 1:208–221 (1971) and in U.S. Pat. No. 3,236,732. Another well-known method of incorporating the desired immunochemically active substance with a carrier material is by contacting the carrier material with tannic acid, glutaraldehyde, formaldehyde, or pyruvaldehyde and thereafter adsorbing the immunochemically active substance to the treated carrier material.

It has also been found that certain passive hemagglutination reactions are optimized by maintaining the pH of the inhibition reaction mixture within a particular pH range by the use of a buffer. It is therefore preferable for optimal performance that a buffer be included in the reaction mixture to control the pH thereof. Moreover, certain ferricspecific chelating agents, most notably N,N-bis-2-hydroxy-ethylglycine, may comprise one of the components of such buffer.

The present invention is applicable to immunochemical assay methods for detecting any antigen or antibody which is adaptable to a passive hemagglutination test format. Exemplary of substances which may be detected according to the present invention are the following antigens and their antibodies: chorionic gonadotropin, luteinizing hormone, human placental lactogen, myoglobin, hemoglobin, and hepatitis B and rubella antigens.

Examples of known passive hemagglutination test methods and the components used therein are disclosed in U.S. Pat. Nos. 3,548,051 and 3,639,558. The immunological reagents and the methods of preparation thereof, the methods of isolating antisera, the methods of combining the test sample, the counterpart component, the indicator component, and so forth which are disclosed in the prior art may be used in the present method.

The present invention will now be illustrated, but is not intended to be limited, by the following examples.

EXAMPLE 1

Preparation of Test Materials

Antisera to human chorionic gonadotropin was prepared according to the method described in the U.S. Pat. No. 3,453,363. An immunological indicator comprising human chorionic gonadotropin chemically coupled to formalinized sheep erythrocytes was prepared according to the method described in U.S. Pat. No. 3,236,732. The resulting sensitized conjugate was resuspended at a concentration of 1.75% W/W in an aqueous solution containing 0.11% diethylbarbituric acid, 0.07% sodium diethylbarbiturate, 1.6% sodium chloride, and 6.0% sucrose. A predetermined amount of antiserum to human chorionic gonadotropin, the amount being appropriate for the particular titer of human chorionic gonadotropin being tested for, was diluted in an aqueous solution containing 0.06% diethylbarbituric acid, 0.04% sodium diethylbarbiturate, 0.85% sodium chloride, 2% sucrose, and 2% rabbit serum to form an antiserum dilution mixture. A 0.25 ml. volume of the indicator suspension was dispensed into the shallow well of a reaction capsule, such as that described in U.S. Pat. No. 3,415,361, and prechilled to about −80° F. A 0.4 ml. volume of the antiserum dilution mixture was dispensed into the deep well of the prechilled reaction capsule. The contents of the test capsule were then lyophilized to a moisture content of less that 2%.

EXAMPLE 2

It is demonstrated in this Example that substantially fewer false negative results are observed in a passive hemagglutination test for human chorionic gonadotropin when a ferric-specific chelating agent is included in the test reaction mixture than when a calcium chelating agent or no chelating agent is included therein.

a. Control Method

One drop of water and one drop of urine to be tested were placed in a test capsule prepared as in Example 1. The capsule was sealed tight, shaken vigorously, and let stand for about one hour. The pattern which resulted was assigned a value as follows:

| Pattern Observed | Value Assigned |
| --- | --- |
| tight, solid disc formed of indicator sediment | 0 |
| dark, clearly distinguishable indicator sediment ring | 1 |
| ring of intermediate darkness | 2 |
| barely distinguishable indicator sediment ring | 3 |
| no percievable ring - smooth hemagglutination deposit | 4 |

In clinical use, a positive test for chorionic gonadotropin is indicated by a pattern having a value of 3 or less. A pattern having a value of 4 indicates a negative test for chorionic gonadotropin.

b. Calcium Chelating Agent Method

The method described in procedure (a) above was followed using one drop of 0.1M ethylenediamine tetraacetic acid (EDTA) solution in place of the drop of water. Within the normal pH range for urine, between about 4 and 8, the affinity of EDTA for ferric ions is less than that for calcium ions.

c. Ferric-Specific Chelating Agent Method

The method described in procedure (b) above was followed using one drop of 0.05M N,N-bis-2-hydroxyethylglycine (referred to herein as BICINE) solution.

Twenty-seven urine samples were tested according to procedures (a), (b), and (c) above. The pH of the samples was also determined. A passive hemagglutination inhibition titration was also performed on each sample to determine chorionic gonadotropin (HCG) level (International units/ml). The results were as follows:

TABLE 1

| Sample No. | pH of Sample | Pattern Observed Control | EDTA | BICINE | HCG level I.U./ml |
|---|---|---|---|---|---|
| 1  | 5   | 4 | 4 | 4 | 0     |
| 2  | 5   | 3 | 3 | 2 | 30    |
| 3  | 5   | 3 | 4 | 3 | 2     |
| 4  | 5   | 2 | 4 | 2 | 20    |
| 5  | 5   | 3 | 3 | 3 | 35    |
| 6  | 5   | 4 | 4 | 3 | 25-30 |
| 7  | 5   | 4 | 3 | 3 | 0-2   |
| 8  | 5   | 2 | 4 | 3 | 20    |
| 9  | 5   | 3 | 4 | 3 | 35    |
| 10 | 7   | 4 | 3 | 3 | 15-20 |
| 11 | 6.5 | 4 | 3 | 3 | 3     |
| 12 | 8   | 4 | 3 | 4 | 25-30 |
| 13 | 7   | 3 | 2 | 3 | 35    |
| 14 | 5   | 3 | 4 | 3 | 25    |
| 15 | 7   | 4 | 4 | 3 | 15-20 |
| 16 | 5   | 3 | 4 | 3 | 3-5   |
| 17 | 8   | 4 | 4 | 4 | 3-5   |
| 18 | 7   | 4 | 3 | 3 | 20    |
| 19 | 7   | 4 | 4 | 3 | 20-25 |
| 20 | 8   | 4 | 3 | 4 | 15-20 |
| 21 | 7   | 4 | 2 | 3 | 35-40 |
| 22 | 7   | 4 | 3 | 4 | 20-25 |
| 23 | 5   | 4 | 3 | 3 | 35    |
| 24 | 7   | 4 | 3 | 3 | 25    |
| 25 | 4   | 3 | 4 | 3 | 15-20 |
| 26 | 5   | 4 | 4 | 3 | 15-20 |
| 27 | 5   | 4 | 4 | 4 | 0-2   |

Considering an HCG level of more than 2 I.U./ml as indicative of pregnancy, the incidence of false negative results were as follows:

TABLE 2

| Total number of Samples | Control | False Negatives EDTA | BICINE |
|---|---|---|---|
| 27 | 14 | 12 | 4 |

The four false negative results using the ferric-specific chelating agent BICINE occurred in Sample Numbers 12, 17, 20, and 22 which had pH levels of 8, 8, 8, and 7 respectively. By adjusting the pH of the urine below 7 during the test reaction, the incidence of false negatives using BICINE was essentially eliminated. From the data it is clear that the incidence of false negatives when BICINE was used was much less than when EDTA was used. From the data listed in Table 1 above it can be seen that even where positives are found by both the BICINE and EDTA methods, the BICINE method generally gave a more distinct indicator sediment pattern.

EXAMPLE 3

Several alternative test systems are illustrated in this Example for the determination of human chorionic gonadotropin using a passive hemagglutination test method. The results observed in all cases were comparable to the results observed following procedure (c) of Example 2.

Alternative Methods A

Test capsules were prepared according to the procedure set forth in Example 1. The test method of procedure a. in Example 2 was followed except that in place of the drop of water a drop of one of the following ferric-chelating agent solutions was used:
1. 1.0M N,N-bis-2-hydroxyethylglycine,
2. 0.05M N,N-bis-2-hydroxyethylglycine and 0.2M morpholinoethane sulfonic acid adjusted to pH with sodium hydroxide,
3. 0.3% o-phenanthroline,
4. 0.05% apoferritin,
5. 0.05% transferrin,
6. 0.05M N,N-bis-2-hydroxyethylglycine and 0.05M phosphate buffer at pH 6, or
7. 0.05M N,N-bis-2-hydroxyethylglycine and 0.2M maleate buffer at pH 6.

Alternative Method B

Test capsules were prepared as in Example 1 except that the diethylbarbituric acid, sodium diethylbarbiturate, and sodium chloride constituents of the antiserum dilution mixture were replaced with 0.05M N,N-bis-2-hydroxyethylglycine and 0.2M morpholinoethane sulfonic acid adjusted to pH 6 with sodium hydroxide. The test method set forth in procedure (a) of Example 2 was followed.

Alternative Methods C

Test capsules were prepared as in Example 1 except that one of the following ferric-specific chelating agent solutions was added to the antiserum dilution mixture:
1. 0.4M N,N-bis-2-hydroxyethylglycine,
2. 0.05% apoferritin, or
3. 0.03% o-phenanthroline The test method set forth in procedure (a) of Example 2 was followed.

It was demonstrated therefore that in accordance with the present invention various ferric-specific chelating agents in various test formats may be used to provide improved test results, characterized primarily by fewer false negative results as compared to the prior art test systems and methods.

What is claimed is:

1. In a method for detecting an immunochemically active substance in a fluid sample by a passive hemagglutination test reaction, the improvement which comprises including in said test reaction a ferric-specific chelating agent.

2. A method as in claim 1 wherein the value of the expression $$\frac{\log K_{Fe}+3}{\log K_{Ca}+2}$$

for said ferric-specific chelating agent is greater than about 7, $\log K_{Fe}+3$ and $\log K_{Ca}+2$ being the stability constants for the complexes formed by the chelating agent with ferric ion and calcium ion, respectively.

3. A method as in claim 1 wherein said ferric-specific chelating agent is selected from the group consisting of phenanthroline, apoferritin, transferrin, deferoxamine, and N,N-bis-2-hydroxyethylglycine.

4. A method as in claim 1 wherein said ferric-specific chelating agent is N,N-bis-2-hydroxyethylglycine.

5. A method as in claim 1 wherein the pH of said test reaction is maintained within a predetermined pH range.

6. A method as in claim 5 wherein said pH is maintained by a buffer.

7. A method as in claim 6 wherein said ferric-specific chelating agent also has buffering capacity.

8. A method as in claim 1 wherein said immunochemically active substance is selected from the group consisting of chorionic gonadotropin, luteinizing hormone, human placental lactogen, myoglobin, hemoglobin, and hepatitis B and rubella antigens.

9. A method as in claim 1 wherein said immunochemically active substance is chorionic gonadotropin.

10. A method as in claim 1 wherein said immunochemically active substance is detected by direct passive hemagglutination wherein said test reaction comprises a passive hemagglutination indicator which includes an immunochemical counterpart of said immunochemically active substance.

11. A method as in claim 1 wherein said immunochemically active substance is detected by passive hemagglutination inhibition wherein said test reaction comprises an immunochemical counterpart of said immunochemically active substance and a passive hemagglutination indicator which includes said immunochemically active substance to be detected.

12. A test composition for detecting an immunochemically active substance in a fluid sample comprising a passive hemagglutination indicator and a ferric-specific chelating agent, said indicator comprising an immunochemical counterpart of said immunochemically active substance.

13. A test composition as in claim 12 wherein the value of of the expression $$\frac{\log K_{Fe}+3}{\log K_{Ca}+2}$$

for said ferric-specific chelating agent is greater than about 7, $\log K_{Fe}+3$ and $\log K_{Ca}+2$ being the stability constants for the complexes formed by the chelating agent with ferric ion and calcium ion, respectively.

14. A test composition as in claim 12 wherein said ferric-specific chelating agent is selected from the group consisting of phenanthroline, apoferritin, transferrin, deferoxamine, and N,N-bis-2-hydroxyethylglycine.

15. A test composition as in claim 12 wherein said ferric-specific chelating agent is N,N-bis-2-hydroxyethylglycine.

16. A test composition as in claim 12 which additionally comprises a buffer.

17. A test composition as in claim 16 wherein said ferric-specific chelating agent also has buffering capacity.

18. A test composition for detecting an immunochemiccally active substance in a fluid sample comprising an immunochemical counterpart of said immunochemically active substance, a passive hemagglutination indicator, and a ferric-specific chelating agent, said indicator comprising said immunochemically active substance.

19. A test composition as in claim 18 wherein the value of the expression $$\frac{\log K_{Fe}+3}{\log K_{Ca}+2}$$

for said ferric-specific chelating agent is greater than about 7, $\log K_{Fe}+3$ and $\log K_{Ca}+2$ being the stability constants for the complexes formed by the chelating agent with ferric ion and calcium ion, respectively.

20. A test composition as in claim 18 wherein said ferric-specific chelating agent is selected from the group consisting of phenanthroline, apoferritin, transferrin, deferoxamine, and N,N-bis-2-hydroxyethylglycine.

21. A test composition as in claim 18 wherein said ferric-specific chelating agent is N,N-bis-2-hydroxyethylglycine.

22. A test composition as in claim 18 which additionally comprises a buffer.

23. A test composition as in claim 22 wherein said ferric-specific chelating agent also has buffering capacity.

24. A test composition as in claim 18 wherein said immunochemically active substance to be detected is chorionic gonadotropin.

25. In a composition comprising a passive hemagglutination indicator dispersed in an aqueous medium, the improvement which comprises including in said composition a ferric-specific chelating agent.

26. A composition as in claim 25 wherein said ferric-specific chelating agent is selected from the group consisting of phenanthroline, apoferritin, transferrin, deferoxamine, and N,N-bis-2-hydroxyethylglycine.

27. A composition as in claim 25 wherein said passive hemagglutination indicator comprises a carrier material and an immunochemically active substance attached thereto, said carrier material being selected from the group consisting of red blood cells and treated red blood cells.

28. A composition as in claim 27 wherein said immunochemically active substance is covalently bound to said carrier material.

* * * * *